United States Patent
Vadakkan

(10) Patent No.: US 9,850,518 B2
(45) Date of Patent: Dec. 26, 2017

(54) BIOMARKERS FOR RAPID DETECTION OF AN OCCURRENCE OF A STROKE EVENT

(71) Applicant: University of Manitoba, Halifax (CA)

(72) Inventor: Kunjumon Ittira Vadakkan, Halifax (CA)

(73) Assignee: Kunjumon Ittira Vadakkan, Halifax, Nova Scotia (CA)

( * ) Notice: Subject to any disclaimer, the term of this patent is extended or adjusted under 35 U.S.C. 154(b) by 0 days.

(21) Appl. No.: 14/761,280

(22) PCT Filed: Jan. 15, 2014

(86) PCT No.: PCT/CA2014/050023
§ 371 (c)(1),
(2) Date: Jul. 15, 2015

(87) PCT Pub. No.: WO2014/110674
PCT Pub. Date: Jul. 24, 2014

(65) Prior Publication Data
US 2015/0344933 A1  Dec. 3, 2015

Related U.S. Application Data

(60) Provisional application No. 61/752,888, filed on Jan. 15, 2013.

(51) Int. Cl.
*C12Q 1/25* (2006.01)
*G01N 21/78* (2006.01)
*G01N 33/49* (2006.01)
*C12Q 1/48* (2006.01)

(52) U.S. Cl.
CPC .............. *C12Q 1/25* (2013.01); *C12Q 1/48* (2013.01); *G01N 21/78* (2013.01); *G01N 33/491* (2013.01); *G01N 2333/9015* (2013.01); *G01N 2333/91074* (2013.01); *G01N 2800/2871* (2013.01)

(58) Field of Classification Search
CPC . C12Q 1/25; C12Q 1/48; G01N 21/78; G01N 2333/9015; G01N 2333/91074; G01N 2800/2871; G01N 33/491; G01N 33/049; G01N 3/063
See application file for complete search history.

(56) References Cited

U.S. PATENT DOCUMENTS 7,427,490 B2  9/2008  Valkirs et al.
7,608,406 B2  10/2009  Valkirs et al.

*Primary Examiner* — Debbie K Ware
(74) *Attorney, Agent, or Firm* — Winstead PC

(57) ABSTRACT

A diagnostic assay for detecting an occurrence of a stroke event in a mammalian subject. The assay comprises the steps of: (i) separating a plasma fraction from a blood sample collected from the mammalian subject; (ii) quantifying in the plasma fraction a L-glutamine hydroxylamine glutamyl transferase (L-GHGT) activity; (iii) quantifying in the plasma fraction a gamma glutamyl hydroxamate synthetase (GGHS) activity; (iv) adding together or alternatively calculating the combinatorial probability for the quantified L-GHGT activity and the quantified GGHS activity to produce a value for the net glutamine synthetase activity, and (v) correlating the net glutamine synthetase activity value with net glutamine synthetase activity values from healthy subjects to detect an occurrence of a stroke event in the mammalian subject. Also disclosed are kits comprising reagents and instructions for performing a diagnostic assay to detect and quantify L-GHGT activity and/or GGHS activity.

5 Claims, 6 Drawing Sheets

BIOMARKERS FOR RAPID DETECTION OF AN OCCURRENCE OF A STROKE EVENT

TECHNICAL FIELD

The present disclosure pertains to the fields of neurology and medicine. More particularly, the present disclosure relates to biomarkers, kits comprising the biomarkers and their use for detecting and/or diagnosing the occurrence of ischemic stroke events.

BACKGROUND

Ischemic stroke events are clinical manifestations of rapid loss in brain functions as a result of a lack of blood supply to the brain region due to blockages in the vascular system exemplified by thrombosis and arterial embolisms. A transient episode of ischemia causing neurological dysfunctions for a short period of time, usually less than 24 hours, is called transient ischemic attack (TIA). Rapid diagnosis and treatment of ischemic strokes can ameliorate long-term debilitating neurological damage responsible for partial or full paralysis of limbs and musculature, and/or cognitive impairments.

Common diagnostic procedures for clinical diagnosis of ischemic stroke include the use of un-infused computerized axial tomographic (CT) imaging and CT angiogram imaging to exclude intra-cerebral hemorrhage and other brain pathologies such as tumors and vascular abnormalities. The limitation with imaging studies is that only a very small percentage of cases of ischemic strokes show any change within the time window of 4.5 hours from the time of onset of stroke symptoms, a critical period during which clot-dissolving medications are useful in dissolving the clot. Therefore, in the majority of cases, a diagnosis of ischemic stroke is made by a reasonable assumption based on clinical presentations. There are numerous diseases that mimic stroke events as their presenting features. They are called stroke-mimics and include diseases exemplified by Todd's paralysis, migraine with prolonged aura, focal neurological deficits associated with hypoglycemia, and hypertensive and metabolic encephalopathies. Currently there are no quick methods available for identification of stroke-mimetic diseases for the purpose of excluding such diseases, and for making a confirmed diagnosis of ischemic stroke in an emergency presentation. Therefore, it is not clear whether all the patients that are diagnosed with ischemic stroke are actually suffering from this clinical condition. Even though magnetic resonance imaging (MRI) scans are available for clinical use, they are even more time-consuming, costly and therefore not used routinely for diagnostic purposes in emergency clinical settings.

An ischemic stroke event results in the death of brain cells at the core of the ischemic area with spread of ischemic changes to the surrounding penumbral area as the duration of the lack of blood supply to the affected regions of the brain increases. The penumbral tissue is potentially amenable to salvage by restoring blood flow. A common emergency treatment strategy to restore blood flow to the brain after an ischemic stroke is to administer intravenous infusion of tissue plasminogen activator (tPA) for augmenting dissolution of the already formed blood clots, preferably within four and a half hours after the onset of symptoms. Currently, emergency treatment protocols for strokes with different volumes of ischemic penumbra deliver the same amount of clot dissolving agent tPA per kilogram of body weight. In other words, the dosages of tPA prescribed are not based on the volume of ischemic penumbra. Moreover, tPA has very serious hemorrhagic side effects and therefore, its indiscriminate use in stroke-mimic cases is not desirable.

Clinical researchers have assessed a wide range of biomolecules released from damaged brain tissue for their potential utility as molecular markers for rapid diagnostic test for stroke events. For example, it is known by those skilled in these arts that biomolecules assessed for their potential usefulness as stroke biomarkers include glial fibrillary acidic protein, protein S-100B, myelin basic protein, C-reactive protein, neuron-specific enolase, S100β, soluble thrombomodulin, capsase 3, tau protein, fatty acid protein, nucleic acids, autoantibodies to N-methyl D-aspartic acid, metalloproteinase-9, L-arginine, plasma glutamate levels, pro-inflammatory cytokines, neuro-inflammatory markers, and interleukin-6 among others. Additionally, the usefulness of detecting and measuring Parkinson 7 protein and nucleoside diphosphate kinase A in cerebrospinal fluid was examined. However, a comparative study by Jauch et al. (2006, *Association of serial biochemical markers with acute ischemic stroke: the National Institute of Neurological Disorders and Stroke recombinant tissue plasminogen activator Stroke Study*. Stroke 37:2508-2513) concluded that none of the biomarkers referred to above were found to be sufficiently reliable for use in clinical medicine, and the authors were unable to identify a clinically useful biomarker for rapid detection of the occurrence of a stroke event.

SUMMARY

The exemplary embodiments of the present disclosure pertain to biomarkers useful for rapid detection of occurrence of stroke events, to methods for use of the biomarkers for rapid detection of occurrence of stroke events, and to kits comprising the biomarkers for use in emergency response and in other clinical situations.

DESCRIPTION OF THE DRAWINGS

The present disclosure will be described in conjunction with reference to the following drawings in which.

DETAILED DESCRIPTION

Figure 1:
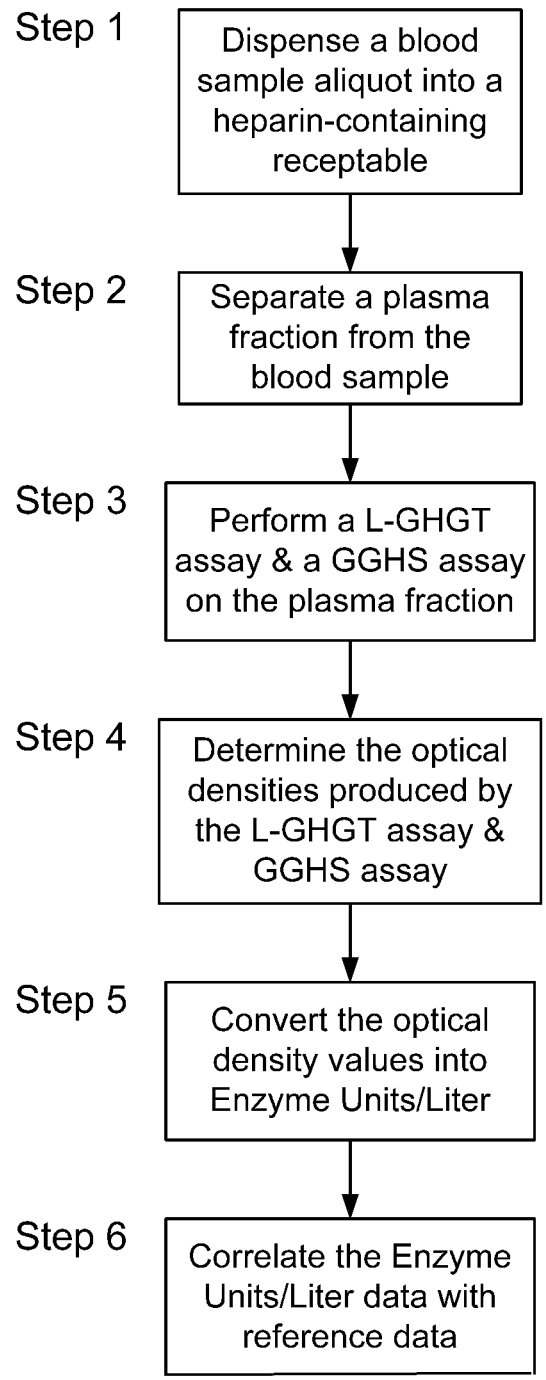
FIG. 1 is a schematic flow chart showing the steps of an exemplary method of the present disclosure for rapid detection of an ischemic stroke event.

Unless otherwise defined, all technical and scientific terms used herein have the same meaning as commonly understood by one of ordinary skill in the art to which this disclosure belongs. In order that the disclosure herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The phrases "prevention of" and "preventing" include the avoidance of the onset of a disease, disorder, or a symptom thereof.

The term "subject" as used herein includes all mammalian members of the animal kingdom, and specifically includes humans.

The terms "about" or "approximately" as used herein, mean within about 25%, preferably within about 20%, preferably within about 15%, preferably within about 10%, preferably within about 5% of a given value or range.

The term "astrocytes" as used herein means the characteristically star-shaped glial cells that are the most abundant cell comprising the human brain. Astrocytes perform many functions, including biochemical support of endothelial cells that form the blood-brain barrier, provision of nutrients to the nervous tissue, and maintenance of extracellular ion balance.

The term "astrocytic perivascular endfeet" as used herein means long foot-like projection from astrocytes that wrap around the capillaries of the vascular system ramifying through the brain.

The term "glial cells" as used herein means non-neuronal cells that maintain homeostasis, form myelin, and provide support and protection for neurons in the brain.

The term "stroke" as used herein means an occurrence of a disturbance in the supply of blood to a mammalian subject's brain that results in rapid loss of brain functions exemplified by an inability to move one or more limbs and/or inability to perceive sensations and/or an inability to understand or formulate speech and/or loss of sight in one or both eyes. The neurological damage caused by the disturbance in supply of blood to the brain may be temporary or permanent, depending on the severity of the disturbance and on how quickly medical intervention was provided.

The term "ischemic stroke" as used herein means a stroke resulting from a lack of blood flow to the brain caused by a blockage(s) in the vascular system supplying the brain. The blockages may be due to one or more of a thrombosis, an embolism, and/or a systemic hypoperfusion.

The term "hemorrhagic stroke" as used herein means a stroke resulting from a rapid accumulation of blood within or about the brain within the skull whereby the increased pressure exerted by the accumulated blood interferes with blood flow to and through the brain.

The term "plasma" as used herein means the fluid portion of the blood in which are suspended the leukocytes, erythrocytes, and platelets.

The term "serum" as used herein means blood plasma with the blood clotting proteins removed.

The term "golden hour" as used herein means the time period, commonly referred to by emergency medical personnel, that lasts from a few minutes to about an hour following a stroke, during which there is the highest likelihood that prompt medical treatment will prevent permanent neurological defects.

The following abbreviations are provided and used herein.

ASPECTS=Alberta Stroke Program Early Computed Tomography Score
ADP=adenosine diphosphate
ATP=adenosine triphosphate
CT=computerized tomography
C=control
CB=control blank
° C.=degrees Celsius
EC=enzyme classification
ELISA=enzyme linked immunosorbent assay
Eq=equation
$FeCl_3$=ferric chloride
g=g force, unit of relative centrifugal force
GGHS=gamma glutamyl hydroxamate synthetase
GS=glutamine synthetase enzyme
hr=hour
HCl=hydrochloric acid
kD=kilo Dalton
L-GHGT=L-glutamine hydroxylamine glutamyl transferase
MRI=magnetic resonance imaging
$Mg^{2+}$=magnesium ion
MgATP=magnesium adenosine triphosphate
$Mn^{2+}$=manganese ion
$MnCl_2$=manganese chloride
MW=molecular weight
M=mole
mM=millimolar
μmol=micromole
mL=milliliter
μL=microliter
μM=micromolar
min=minutes
n=number
nm=nanometer
$NH_2OH$=Hydroxylamine
$NH_3$=ammonia
NIHSS=National Institute of Health stroke scale
N=normal
OD=optical density
Pi=inorganic phosphate
s=second
s.e.m.=standard error of the mean
TIA=transient ischemic attack
tPA=tissue plasminogen activator (tPA)
U=units (enzyme units)
U/L=units per liter of plasma Currently, there are no reliable rapid diagnostic tests available for confirmation of the occurrence of a stroke after a clinical observation suggesting a stroke event has made. Accordingly, the exemplary embodiments of the present disclosure pertain to biomarkers that were found to be useful for rapid detection of occurrence of stroke events, to methods for use of the biomarkers for rapid detection of occurrence of stroke events, and to kits comprising the biomarkers for use in emergency response and in clinical situations for rapid detection of occurrence of stroke events.

Capillaries, the smallest blood vessels in the brain, are surrounded by astrocytic perivascular endfeet. The cell interphase between the capillaries and the astrocytic perivascular endfeet is referred to as blood brain barrier. When blood vessels are blocked by a blood clot or by other means, blood flow through the blood vessels reduces and even stops. A sudden cessation of blood flow through the capillaries will cause hypoxic damage to the astrocytes resulting in the leakage of the astrocytic membranes. In other words, the blood brain barrier becomes leaky. The consequence will be a release of astrocytic cytoplasmic constituents into the blood stream. It is also known that astrocytic perivascular endfeet surround the para-vascular spaces that drain into the venous system. It was discovered recently that this paravascular pathway can transport the leaked glutamine synthetase enzyme from the extracellular matrix space to the perivenular space and then to the venous system (Iliff et al. (2012, *A paravascular pathway facilitates CSF flow through the brain parenchyma and the clearance of interstitial solutes, including amyloid β*. Sci. Transl. Med. 4(147):147ra111). Accordingly, it appears that glutamine synthetase enzymes reach the blood steam from the astrocytes during an ischemic stroke event. Therefore, I hypothesised that one or more of astrocytic cytoplasmic constituents if detectable in the peripheral venous blood by simple and fast assay methods, can be used as biomarkers signaling the occurrence of a stroke event.

Enzymes are biological catalysts that do not take part in chemical reactions. Therefore, small amounts of these molecules reaching the blood should be sufficient to specifically catalyze a reaction. The enzyme glutamine synthetase is expected to be constitutively expressed in sufficiently large amounts to enable conversion of glutamate ions transported into the astrocytes from peri-synaptic locations to glutamine. Glutamine synthetase produced in the human brain occurs as an octamer with a molecular weight of 420.65 kD and is dissociated under reducing and denaturing conditions into monomeric subunits having molecular weights of about 44 kD exhibiting biological enzymatic activities. This led to the idea that glutamine synthetase will be leaked into the blood stream in detectable amounts when astrocytic membranes become leaky as a consequence of a stroke event. Since the venous system also receives drainage from para-vascular space that is in close contact with astrocytic perivascular endfeet, this is an additional route of entry for glutamine synthetase enzyme into the systemic circulation. A hypothesis was made that detection of the activities of glutamine synthetase in plasma fractions from blood samples, will be useful biomarkers for detecting the occurrence of stroke events.

There are at least three different methods for detecting and quantifying the enzymatic activity of glutamine synthetase. For example, glutamine synthetase activity can be measured directly by the reaction:

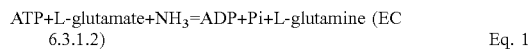

$$\text{ATP} + \text{L-glutamate} + \text{NH}_3 = \text{ADP} + \text{Pi} + \text{L-glutamine (EC 6.3.1.2)} \quad \text{Eq. 1}$$

The amount of ADP or phosphate or L-glutamine produced will be directly proportionate to the amount of glutamine synthetase entering into the blood stream, and can be used in further chemical reactions to quantitate the glutamine synthetase activity.

For example, glutamine synthetase activity can be quantified with monoclonal antibody ELISA assays using methods taught by Takahashi et al. (2002, *Immunoassay for serum glutamine synthetase in serum: development, reference values, and preliminary study in dementias*. Clin. Chem. 48:375-378) and by Tumani et al. (1999, *Glutamine synthetase in cerebrospinal fluid, serum, and brain: a diagnostic marker for Alzheimer disease?* Arch. Neurol. 56:1241-1246).

For example, glutamine synthetase activity can be measured indirectly by assessing other catalytic activities using exogenous substrates that are not normally present in the body. Glutamine synthetase enzyme is known to undergo various post-translational modifications (Shapiro et al., 1967, *Regulation of glutamine synthetase. Adenyl glutamine synthetase: a new form of the enzyme with altered regulatory and kinetic properties*. Proc. Nat. Acad. Sci., 58(2):642-649; Tate et al., 1971, *Regulation of rat liver glutamine synthetase: activation by alpha-ketoglutarate and inhibition by glycine, alanine, and carbamyl phosphate*. Proc. Nat. Acad. Sci., 68(4):781-785; Eisenberg et al., 2000, *Structure-function relationships of glutamine synthetases*. Biochim Biophys Acta. 1477(1-2):122-145). Adenylation is the commonest type of modification across different species of animals, and it is known that adenylated and non-adenylated forms of the enzyme have different substrate specificities. However, all of the factors that determine the modification-state of the enzyme at a given time are not known and it is likely that large numbers of factors can influence the post-translational modifications of the enzyme. In order to quantitate total glutamine synthetase activity, it is necessary to measure the activities of its various forms.

It was surprisingly discovered that L-glutamine hydroxylamine glutamyl transferase (L-GHGT) activities and gamma glutamyl hydroxamate synthetase (GGHS) activities can be detected in plasma fractions separated from blood samples collected from human subjects. Furthermore, it was have discovered that the combined activities of L-GHGT and GGHS which provide a combined measure of activities of the different post-translationally modified forms of the enzyme glutamine synthetase, are present in significantly higher amounts in patients who have experienced an ischemic stroke event when compared to control patients. Accordingly, the exemplary embodiments of the present disclosure pertain to the use L-GHGT and GGHS as biomarkers for rapid detection of occurrence of stroke events, to compositions comprising the biomarkers for use in the detection of stroke events, to assays wherein the biomarkers are used for rapid detection of occurrence of stroke events, and to kits comprising the biomarkers for use in emergency response and in clinical situations for rapid detection of occurrence of stroke events.

The exemplary rapid diagnostic assays of the present disclosure for the detection of stroke events are based on assaying blood samples from mammalian subjects to detect the presence of glutamine synthetase catalytic activities L-glutamine hydroxylamine glutamyl transferase (L-GHGT) and gamma glutamyl hydroxamate synthetase (GGHS).

The initial steps in carrying out the rapid diagnostic assays of the present disclosure comprise collection of blood sample from subjects and separation of the blood into its cellular and plasma fractions. Aliquots of blood sample are dispensed into lithium heparin tubes which are then centrifuged to separate the blood into a plasma fraction and a fraction comprising the leukocytes, erythrocytes, and platelets. While it is preferable to use lithium heparin tubes for separation of the blood fractions, a skilled person will appreciate that various other anticoagulants known to them can be used to obtain the plasma. The separated plasma fractions can then be used to perform the L-GHGT activity assays and the GGHS activity assays for detection of the glutamine synthetase enzyme following the steps disclosed herein. It should be noted that while it is preferred to use plasma fractions with the present methods, it is also suitable to perform the methods disclosed herein using serum fractions prepared from blood samples.

It should be noted that in the methods described in detail below, all reagents are dissolved in water unless otherwise specified. The assays use L-glutamate at its maximal concentration in water. To prepare 0.05M solution of L-glutamate, the solution should be warmed and then shaken for several minutes. All reagents can be stored at 20° C. except for L-glutamine, NaADP, and MgATP, which should be stored at temperatures from the range of about 4° C. to about 8° C. FeCl$_3$ should be stored away from light and air. All reagents including plasma should be brought to 20° C. before performing the assays.

The rapid diagnostic assays of the present disclosure generally comprise the following steps:

Step 1: Detection of L-GHGT Catalytic Reactions and GGHS Catalytic Reactions (i) Detection of L-GHGT activity occurs by the reaction:

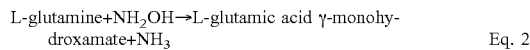

$$\text{L-glutamine} + NH_2OH \rightarrow \text{L-glutamic acid } \gamma\text{-monohydroxamate} + NH_3 \qquad \text{Eq. 2}$$

at about 30° C. using $Mn^{2+}$ and ADP as catalysts.

The product L-glutamic acid γ-monohydroxamate is also known as γ-glutamyl hydroxamate. In an exemplary assay, the optimum ratios of volumes of the reagents in the reaction are carried out by mixing them using the same units of volume. The concentrations of reagents and ratios of volumes of reagents are optimized based on the maximum solubility of the reagents and the optimum ratios of reagents for reactions. The optimal concentrations and the ratios of the reagents to be mixed immediately before the reaction for the maximal formation of the product L-glutamic acid γ-monohydroxamate in the reactions were determined as follows. All volumes are taken in the same units throughout the entire assay.

Imidazole buffer (0.5M; pH 6.5):NH$_2$OH (0.4M):L-glutamine (0.1M):MnCl$_2$ (0.03M):NaADP (0.01M)=20:15:60:5:5. This results in a total volume of 105 volume units for each of the "test" mixture and the "control" mixture. The reaction in the control test tube is prevented by sequentially adding the inhibitors L-methionine sulfoximine (0.05M) and HCl (2N) and mixing well after each addition.

The optimum ratios of volumes of the initial reaction mixture, L-methionine sulfoximine and HCl in the control reaction are determined as follows. All volumes should be taken in the same units. Reaction mixture:L-methionine sulfoximine (0.05M):HCl (2N) in the control reaction=105:10:20. To the test solution, double distilled water is added at optimum ratios of volumes of the initial reaction mixture to water as 105:30. All volumes should be taken in the same units. At this time, the reaction mixture including the inhibitors has a volume of 135 volume units. In the next step, plasma is added to both the tubes marked "test" and "control" at a ratio of reaction mixture:plasma=135:50 using the same unit of volume used for addition of all other reagents. The total volume in each "test" tube and "control" tube is 185 volume units. The final reaction mixture is incubated at 30° C. for 5 minutes.

After the incubation period is completed, the enzyme activity is stopped in the "test" mixture by sequentially adding L-methionine sulfoximine (0.05M) and HCl (2N) and mixing well after each addition. The optimum ratio of volumes of final reaction mixture, L-methionine sulfoximine (0.05M) and HCl (2N), in the "test" reaction is as follows. All volumes should be taken in the same units. Final reaction mixture:L-methionine sulfoximine (0.05M):HCl (2N) in the "test" reaction=185:10:20. To the "control" reaction mixture, double distilled water is added at an optimum ratio of volumes as follows. The "control" final reaction mixture:water ratio=185:30. All volumes are taken in the same units. The total volume is 215 volume units in each of the "test" tubes and "control" tubes. While the disclosed concentrations and ratios are preferred, those skilled in this art will understand that various other combinations of reagent concentrations and volumes can be used to carry out the present assays.

(ii) Detection of GGHS activity occurs by the reaction:

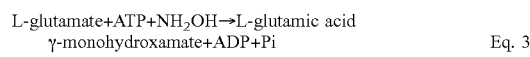

$$\text{L-glutamate} + ATP + NH_2OH \rightarrow \text{L-glutamic acid } \gamma\text{-monohydroxamate} + ADP + Pi \qquad \text{Eq. 3}$$

at about 37° C. using $Mg^{2+}$ as the catalyst.

The product L-glutamic acid γ-monohydroxamate is also known as γ-glutamyl hydroxamate. In an exemplary assay, the optimum ratios of volumes of the reagents in the reaction are carried out by mixing them immediately before the reaction using the same units of volume. The concentrations of reagents and the ratios of volumes of reagents are optimized based on the maximum solubility of the reagents and the optimum ratios of reagents for reactions. For the optimal formation of the product L-glutamic acid γ-monohydroxamate, reagents are added to the "test" solutions and "control" solutions at a ratio as follows. All volumes are taken in the same units throughout the entire assay.

Imidazole buffer (0.5 M) pH 7.2:NH$_2$OH (0.4 M):L-glutamate (0.05M):MgATP (0.02 M)=20:10:120:5. The total volume=155 volume units. Catalytic reaction in the "control" reaction tube is prevented by sequentially adding L-methionine sulfoximine (0.05M) and HCl (2 N) and mixing well after each addition. The optimum ratio of volumes of reaction mixture, L-methionine sulfoximine (0.05 M) and HCl (2 N) in the "control" reaction are as follows. All volumes should be taken in the same units. Reaction mixture:L-methionine sulfoximine (0.05 M):HCl (2 N) in the "control" reaction=155:10:20. To the "test" reaction mixture, double distilled water is added at an optimum ratio of volumes of initial reaction mixture to water as 155:30. The total volume in both the "test" and "control" tubes is 185 volume units. All volumes should be taken in the same units.

In the next step, plasma is added to each of the tubes marked "test" and "control" at a reaction mixture: plasma ratio=185:50 in the same unit of volume used in adding all other reagents. The total volume in each tube now becomes 235 volume units. The final reaction mixture is incubated at 37° C. for 5 minutes.

After the incubation, enzyme activity is stopped in the "test" reaction tubes by sequentially adding L-methionine sulfoximine and HCl and mixing well after each addition. The optimum ratio of volumes of final reaction mixture, L-methionine sulfoximine and HCl in the "test" reaction is determined as follows. All volumes should be taken in the same units throughout the entire assay. The ratio of the final reaction mixture:L-methionine sulfoximine:HCl in the "test" reaction tube=235:10:20. To the "control" reaction mixture, double distilled water is added at the optimum ratio of volumes of reaction mixture to water, of 235:30. All volumes are taken in the same units. The total volume becomes 265 volume units in each of the "test" reaction tubes and "control" tubes. While the disclosed concentrations and ratios are preferred, those skilled in this art will understand that various other combinations of reagent concentrations and volumes can be used to carry out present assays.

Step 2: Generating Color Reactions with the L-GHGT Reaction Product and GGHS Reaction Product The final common product of both the L-GHGT reactions and the GGHS reactions is L-glutamic acid γ-monohydroxamate. The addition of $FeCl_3$ (2 M) to L-glutamic acid γ-monohydroxamate under acidic conditions causes the formation of a ferric hydroxamate color complex. All volumes are taken in the same units throughout the entire assay. In the L-GHGT activity assay, the ratio of volumes of the final reaction mixture:$FeCl_3$ (2 M)=215:5 in each of the "test" and "control" tubes. In the GGHS activity assay, the ratio of volumes of final reaction mixture:$FeCl_3$ (2 M)=265:5 in each of the "test" and "control" tubes. Each of the L-GHGT and GGHS reaction tubes are incubated at 37° C. for 1 minute for optimum formation of the ferric hydroxamate color complex.

Step 3: Calculation of Optical Densities of the Final Colored Products

The ferric hydroxamate complex, when mixed with plasma, was found to have an absorption maximum to light of wavelength of 500 nm. The net color intensity of the ferric hydroxamate complex is calculated as the net optical density ($OD_{NET}$) by determining the difference between the optical density of the test sample and the optical density of the control sample. For example:

Test sample OD=[OD of test sample−OD of test blank]   Eq. 4

Control sample OD=[OD of control sample−OD of control blank]   Eq. 5

Observations made during numerous experiments conducted during the development of the assays indicated that ODs of test blank are approximately equal to the ODs of control blanks. Therefore, the $OD_{NET}$ can be re-written as $OD_{NET}$=OD of test sample−OD of control sample   Eq. 6

While it is preferred to use the wavelength of 500 nm in the present disclosure, one of skill in the art will appreciate that the maximal optical density of a final colored product in plasma samples can vary between samples. Since both the "test" and the "control" reactions contain the same reagents and plasma, all the factors contributing to the optical density, other than the final product ferric hydroxamate from the L-GHGT and GGHS catalytic activities, are expected to be cancelled out.

Step 4: Standard Curve for the Final Color Product for Estimation of γ-Glutamyl Hydroxamate Formed A standard curve of the optical density of the ferric hydroxamate complex is prepared by freshly made γ-glutamyl hydroxamate (L-glutamic acid γ-monohydroxamate) solutions of serial dilutions ranging from about 2.5 mM to about 39.06 μM. Separate standard reactions are carried out using the reagents contained in the actual L-GHGT and GGHS biomarker assays as described in the assay. Instead of plasma, a 50-unit volume of γ-glutamyl hydroxamate is added.

The graph of optical density plotted on y axis versus concentration of the γ-glutamyl hydroxamate in mM plotted on the x axis is a straight line per the following equation:

$y=mx+b$   Eq. 7 where y=optical density, m=slope of the line, x=concentration of the γ-glutamyl hydroxamate in mM (millimolar), and b is the y-intercept.

Using the optical densities, slope and y-intercept of this straight line, the concentration of γ-glutamyl hydroxamate formed by the L-GHGT and GGHS catalytic activities of glutamine synthetase enzyme is calculated and expressed in μM (micromolar) concentrations. It is to be noted that the values for standard curves will vary slightly from laboratory to laboratory based on the different instruments, reagent quality and experimental conditions used. Therefore, each laboratory should produce its own standard curves.

Step 5: Conversion of γ-Glutamyl Hydroxamate Concentrations to L-GHGT Catalytic Activities and GGHS Catalytic Activities of Glutamine Synthetase Enzyme Expressed as Units Per Liter of the Plasma.

L-GHGT catalytic activities and GGHS catalytic activities are expressed in microkatals as the number of micromoles of γ-glutamyl hydroxamate formed per second. This is then converted into Enzyme Units. One unit of catalytic activity in Enzyme Units=⅙₀th of a microkatal.

$$\text{Catalytic activity in Enzyme Units } (U) = \frac{\gamma\text{-glutamyl hydroamate in } \mu M}{\text{Duration of incubation in seconds} \times 60} \quad \text{Eq. 8}$$

From the standard curve using reagents used in the assays, catalytic activity per liter of plasma expressed in Enzyme units per liter (U/L) is derived.

L-GHGT and GGHS catalytic activities are expressed in Enzyme Units per Liter (U/L) of plasma using the formula:

$$= \frac{\gamma\text{-glutamyl hydroxamate in } \mu M \times 1000 \times 1000}{\text{Duration in cubation in seconds} \times \text{volume of plasma in } \mu L \times 60} \quad \text{Eq. 9}$$

L-GHGT catalytic activities and GGHS catalytic activities of glutamine synthetase enzyme are expected to occur in very small amounts in the plasma of normal subjects as a result of leakage from dying astrocytes in the nervous system and dying platelets in the circulation. It was discovered that the L-GHGT catalytic activities and GGHS catalytic activities of the glutamine synthetase enzyme are significantly elevated in blood samples after the occurrence of a stroke event. While it is the ischemia resulting from ischemic stroke that causes the astrocytic membranes to leak, it is likely that such ischemic changes also occur during hemorrhagic strokes (also known as intra-cerebral hemorrhages). Intra-cerebral hemorrhagic bleeding into the extra-cellular matrix spaces can compress small vessels and capillaries, and result in ischemia of the neighboring areas of the brain.

Plasma samples containing high levels of bilirubin, creatine kinase, myoglobin and those from haemolysed blood are not suitable for this assay. It is known that glucocorticoids induce and vitamin D inhibits the expression and activity of glutamine synthetase (Olkku et al., 2008, *Wnt and steroid pathways control glutamate signalling by regulating glutamine synthetase activity in osteoblastic cells*. Bone, 43(3):483-93). Therefore, it should be noted that blood samples from patients taking steroids of any form or vitamin D, are not suitable for the assays disclosed herein.

It is understood that various other modifications will be apparent to and can be made by those who skilled in the art without departing from the scope and spirit of this disclosure. Some exemplary embodiments pertain to use of the L-GHGT activities and GGHS activities of the glutamine synthetase enzyme from the blood samples in conditions: (i) resulting ischemia from disease conditions other than stroke, and (ii) leakage of blood brain barrier as in traumatic brain injury.

Some exemplary embodiments of the present disclosure are illustrating in the following example generally following the steps shown in FIG. 1. The assays disclosed herein were performed with blood samples collected from patients admitted with stroke symptoms and other acute neurological disorders. The chemicals used were not 100% pure in nature. Various experiments have previously shown that different trace metals can influence the two catalytic activities of the glutamine synthetase enzyme. Therefore, the absolute values that are obtained by using different chemicals from different sources may vary. In order to neutralize the effect of the trace metals in the reactions, the assays were designed such that both the test and control reactions use all the chemical reagents equally. It should be appreciated by those of skill in the art that the absolute values of the enzyme activities may vary when chemicals from different sources are used. However, once a diagnostic assay kit is designed using chemicals from a specific source, population average cut-off values can be determined for both controls and stroke patients that will enable rapid detection of an occurrence of a stroke event. It should be appreciated by those of skill in the art that the techniques disclosed in the example represent techniques discovered by the inventor to function well in the practice of the disclosure, and thus can be considered to constitute preferred modes for its practice.

Example 1

The chemicals used in this example were obtained from Sigma-Aldrich Canada Co. (Oakville, ON. Calif.): (i) imidazole (Sigma product No. 15513), (ii) L-glutamine (Sigma product No. G3126), (iii) $NH_2OH$ (Sigma product No. 467804), (iv) $MnCl_2.4H_2O$ (Sigma product No. 203734), (v) NaADP (Sigma product No. A2754), (vi) MgATP (Sigma; A9187), (vii) L-methionine sulfoximine (Sigma product No. M5379), (viii) $FeCl_3$ (Sigma product No. 701122), and (ix) L-glutamic acid γ-monohydroxamate ((γ-glutamyl hydroxamate) (Sigma product No. G2253)). L-glutamate was obtained from EMD Millopore (Billerica, Mass., USA; Calbiochem product no. 3510).

The L-GHGT Activity Assay:

The first step of the L-GHGT activity assay was to carry out a "test" reaction. This was done by first carrying out the L-GHGT activity for a specific period of time. In the next step, the enzyme reaction was stopped by adding inhibitors of the L-GHGT activity of the glutamine synthetase enzyme. The final product of the L-GHGT activity, namely L-glutamic acid γ-monohydroxamate, was then made to form a colored ferric hydroxamate product. In the next step, the optical density of this colored product was measured at 500 nm. All the reactions are carried out by mixing the solutions in the ratios described in the procedure section. The units of volumes used in this example reaction are in μL.

The "test" reaction was carried out by first dispensing into a tube (i) 20 μL of pH 6.5 imidazole buffer (0.5 M), (ii) 15 μL of $NH_2OH$ (0.4 M), (iii) 60 μL of L-glutamine (0.1 M), (iv) 5 μL $MnCl_2$ (0.03 M), and (v) 5 μL NaADP (0.01 M) and then mixing these reagents together. Then to the mixture was added 30 μL of double distilled water and 50 μL of a plasma sample, followed by mixing. The "test" reaction tube was incubated in a 30° C. water bath for 5 minutes. Then, 10 μL of L-methionine sulfoximine (0.05M) and 20 μL of HCl (2 N) were added to the tube and mixed well. Then, 5 μL of $FeCl_3$ (2 M) is added to the tube and mixed well. The final solution was incubated at 37° C. water bath for 1 minute after which, the optical density of the final "test" solution was read using light of wavelength 500 nm.

The second step of the L-GHGT activity assay is to carry out a "control" reaction for the test assay carried out in the first step. This was done by first carrying out the L-GHGT catalytic activity assay after inhibiting the activity of the glutamine synthetase enzyme. The "control" reaction was carried out by first dispensing into a tube (i) 20 μL of pH 6.5 imidazole buffer (0.5 M), (ii) 15 μL of $NH_2OH$ (0.4 M), (iii) 60 μL of L-glutamine (0.1 M), (iv) 5 μL of $MnCl_2$ (0.03 M), (v) 5 μL of NaADP (0.01 M), and then mixing these reagents together. Then to the mixture was added 10 μL of L-methionine sulfoximine (0.05M) and 20 μL of HCl (2 N) and mix well. Following this, 50 μL of a plasma sample was added to the mixture and then mixed well. The "control" reaction tube was incubated at 30° C. water bath for 5 minutes. Then, 30 μL of water was added to the tube and mixed well after which, 5 μL of $FeCl_3$ (2 M) was added to the tube and mixed well. The final solution was incubated in a 37° C. water bath for 1 minute. The optical density of the final "control" solution mixture was read at 500 nm. All reactions were carried out by mixing the solutions in the ratios described in the previous section. The units of volumes used in the reaction are in μL.

The third step for the L-GHGT assay is to calculate the $OD_{NET}$ for each plasma sample using the equation EQ. 6. By comparing the $OD_{NET}$ data against the standard curve of optical density of the ferric hydroxamate complex, the concentration of γ-glutamyl hydroxamate formed from L-GHGT catalytic activity of the glutamine synthetase enzyme from the plasma sample is calculated and expressed in micromoles. The fourth step is to convert the micromoles of γ-glutamyl hydroxamate formed by the L-GHGT catalytic activity into Units of catalytic activity per Liter (U/L) of plasma using equation EQ. 16.

The GGHS Activity Assay:

The first step of the GGHS activity assay was to carry out a "test" reaction. This was done by first carrying out the GGHS activity assay for a specific period of time to facilitate formation of the reaction product L-glutamic acid γ-monohydroxamate. In the next step, the enzyme reaction was stopped by adding inhibitors of the GGHS activity of the glutamine synthetase enzyme. The final product formed, if any, was then reacted with $FeCl_3$ to form the colored product ferric hydroxamate complex. In the next step, the optical density of this colored complex was measured at 500 nm. All the reactions were carried out by mixing the solutions in the ratios described in the procedure section. The units of volumes used in the example reaction are in microliters.

The "test" reaction was carried out by first dispensing into a tube (i) 20 μL of pH 7.2 imidazole buffer (0.5 M), (ii) 10 μL of $NH_2OH$ (0.4 M), (iii) 120 μL of L-glutamate (0.05 M), and (iv) 5 μL of MgATP (0.02 M) and then mixing these reagents together. Then, to the mixture was added 30 μL of double distilled water and 50 μL of a plasma sample followed by further mixing. The "test" reaction tube was incubated in a 37° C. water bath for 5 minutes after which was added 10 μL of L-methionine sulfoximine (0.05M) and 20 μL of HCl (2 N) and mixed well. Then, 5 μL of $FeCl_3$ (2 M) was added to the tube and mixed well. The final solution was incubated in a 37° C. water bath for 1 minute. The optical density of the final "test" solution was read at 500 nm The second step of the GGHS activity assay was to carry out a "control" reaction for the test assay carried out in the first step. This was done by first carrying out the GGHS activity assay after inhibiting the GGHS activity of the glutamine synthetase enzyme. The final product of the GGHS activity, namely L-glutamic acid γ-monohydroxamate, was then made to form the colored ferric hydroxamate complex. In the next step, the optical density of this colored complex was measured at 500 nm. All the reactions were carried out by mixing the solutions in the ratios described in the previous section. The units of volumes used in the reaction are in microliters.

The "control" reaction was carried out by first dispensing into a tube (i) 20 μL of pH 7.2 imidazole buffer (0.5 M), (ii) 10 μL of NH$_2$OH (0.4 M), (iii) 120 μL of L-glutamate (0.05 M), and (iv) 5 μL MgATP (0.02 M) and then mixing these reagents together. Then to the mixture was added 10 μL of L-methionine sulfoximine (0.05 M) and 20 μL of HCl (2 N) and mixed well. Following this, 50 μL of a plasma sample was added to the mixture and mixed well. The "control" reaction tube was incubated in a 37° C. water bath for 5 minutes after which, 30 μL of water was added to the tube and mixed well. Then, 5 μL of FeCl$_3$ (2 M) was added to the tube and mixed well. The final solution was incubated in a 37° C. water bath for 1 minute. The optical density of the "control" solution mixture was read at 500 nm.

The third step for the GGHS assay was to calculate the OD$_{NET}$ for each plasma sample using equation EQ. 6. By comparing the OD$_{NET}$ data against the standard curve of the optical density of the ferric hydroxamate complex, the concentration of γ-glutamyl hydroxamate formed from GGHS catalytic activity of the glutamine synthetase enzyme from the plasma sample is calculated and expressed in micromoles. The fourth step is to convert the micromoles of γ-glutamyl hydroxamate formed by the GGHS catalytic activity into Units of catalytic activity per Liter (U/L) of plasma using the equation EQ. 18.

Standard Curve for γ-Glutamyl Hydroxamate

Exemplary standard curve values were obtained as follows. A standard curve of the optical density of the ferric hydroxamate complex formed was plotted against the concentration of γ-glutamyl hydroxamate (L-glutamic acid γ-monohydroxamate) in mM. Freshly made γ-glutamyl hydroxamate (L-glutamic acid γ-monohydroxamate) solutions of serial dilutions ranging from 2.5 mM to 39.06 μM were used to make the standard curve.

To make the standard curve for γ-glutamyl hydroxamate in the presence of reagents for L-GHGT activity, the following chemical solutions were mixed together: (i) 20 μL of pH 6.5 imidazole buffer (0.5 M), (ii) 15 μL of NH$_2$OH (0.4 M), (iii) 60 μL of L-glutamine (0.1 M), (iv) 5 μL MnCl$_2$ (0.03 M), and (v) 5 μL NaADP (0.01 M). To this mixture was added 30 μL of double distilled water and 50 μL of the standard solution of γ-glutamyl hydroxamate followed by mixing. The tube containing the reagent mixture was incubated in a 30° C. water bath for 5 minutes. Then, 10 μL of L-methionine sulfoximine (0.05M) was added and mixed well. The final color product ferric hydroxamate complex was developed by adding 20 μL of HCl (2 N) and 5 μL of FeCl$_3$ (2 M) and then mixed well. The reaction was completed by incubation at 37° C. for 1 minute. The optical density of the ferric hydroxamate complex was measured at 500 nm.

For making the standard curve for γ-glutamyl hydroxamate in the presence of reagents for GGHS activity, the following chemical solutions were mixed together: (i) 20 μL of pH 7.2 imidazole buffer (0.5 M), (ii) 10 μL of NH$_2$OH (0.4 M), (iii) 120 μL of L-glutamate (0.05 M), and (iv) 5 μL of MgATP (0.02 M). To this mixture was added 30 μL of double distilled water and 50 μL of the standard solution of γ-glutamyl hydroxamate followed by mixing. The tube containing the reagent mixture was incubated in a 37° C. water bath for 5 minutes. Then, 10 μL of L-methionine sulfoximine (0.05M) was added and mixed well. The final color product ferric hydroxamate complex was developed by adding 20 μL of HCl (2 N) and 5 μL of FeCl$_3$ (2 M) and then mixed well. The reaction was completed by incubation at 37° C. for 1 minute. The optical density of the ferric hydroxamate complex was measured at 500 nm.

Figure 2:
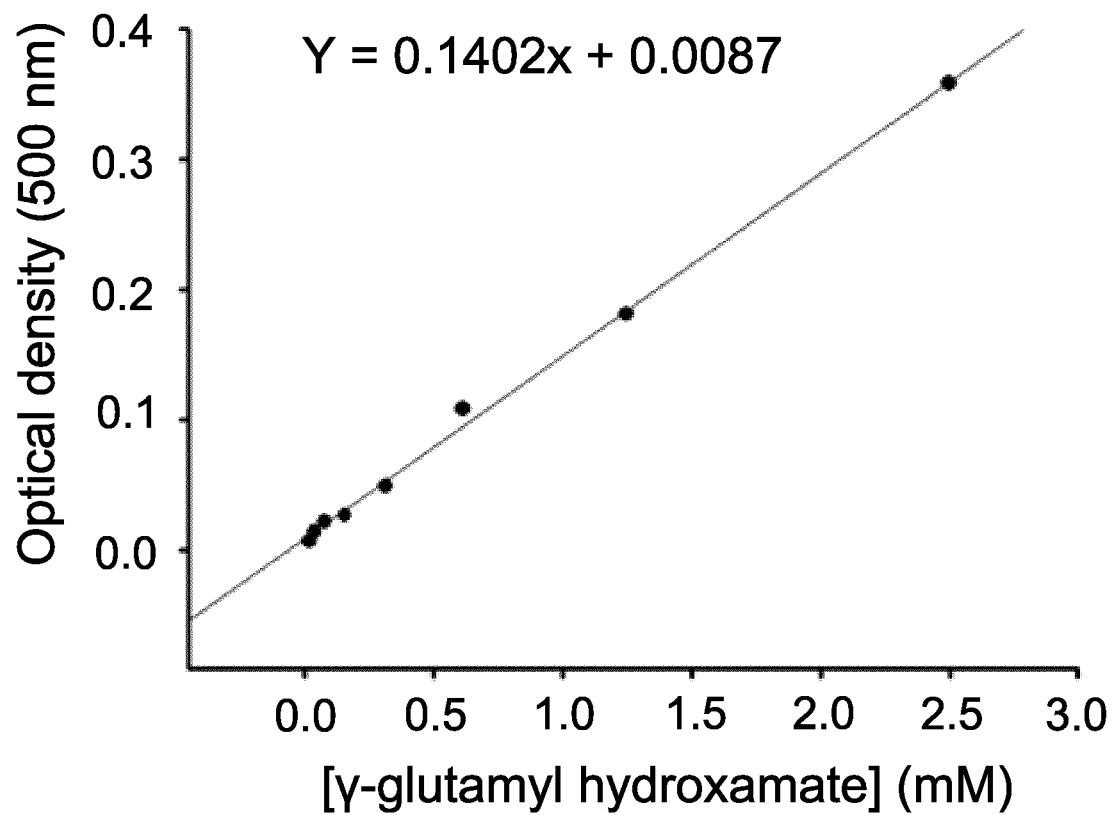
FIG. 2 is a chart showing a standard curve for a ferric hydroxamate complex formed from a reaction of γ-glutamyl hydroxamate with $FeCl_3$ in an acidic medium, in the presence of reagents used for detecting L-GHGT catalytic activity.

Standard curves were plotted for the ferric hydroxamate complex in the presence of reagents used for both the L-GHGT and GGHS catalytic activities. The standard curves were made by plotting the optical density of the colored product ferric hydroxamate on the y axis and the concentration of the γ-glutamyl hydroxamate in mM plotted on the x axis. FIG. 2 shows an exemplary standard curve for ferric hydroxamate complex formed from γ-glutamyl hydroxamate with FeCl$_3$ in acidic medium, in the presence of reagents used in L-GHGT catalytic activity. In reference to Equation 7, the equation of the graph for the standard curve is as follows:

$$y=(0.1402x)+0.0087 \qquad \text{Eq. 10}$$

where y was the optical density at 500 nm of wavelength and x was the concentration of γ-glutamyl hydroxamate in mM. From the Equation 10, the concentration of γ-glutamyl hydroxamate in μM was derived as follows:

$$\gamma\text{-glutamyl hydroxamate in } \mu M = x = \frac{(y - 0.0087) \times 1000}{0.1402} \qquad \text{Eq. 11}$$

Figure 3:
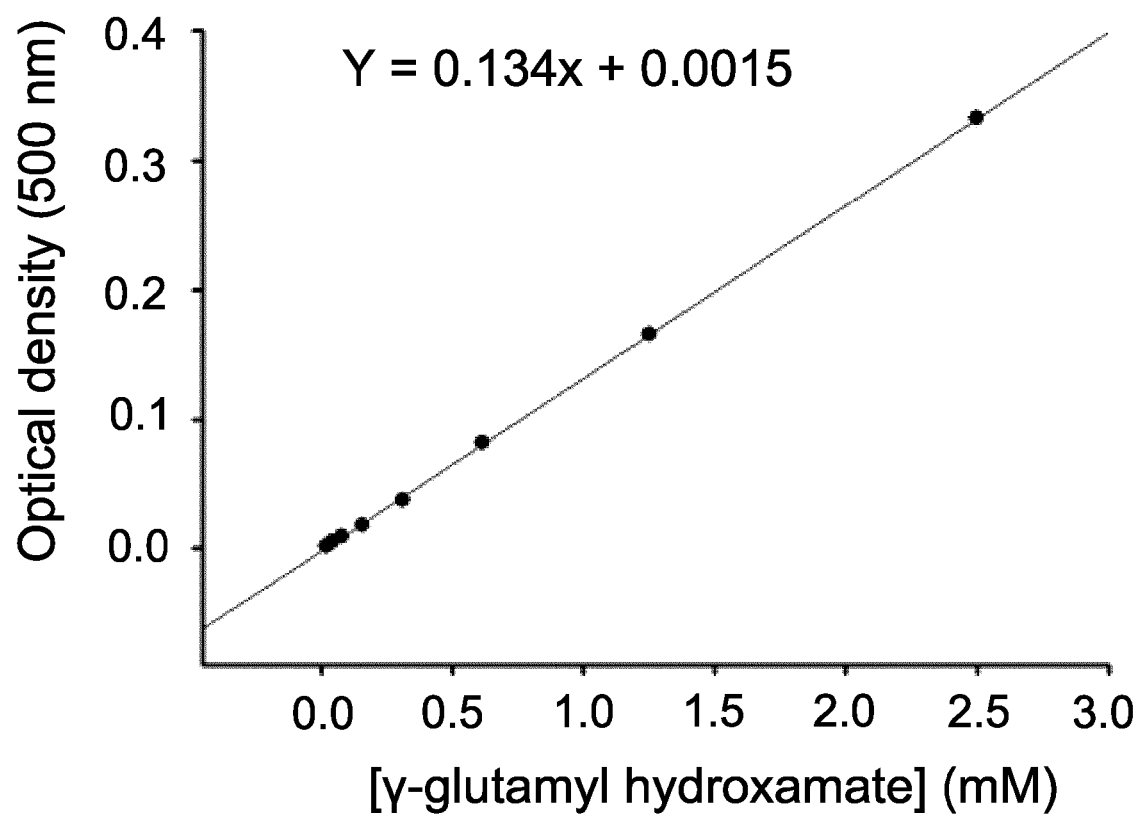
FIG. 3 is a chart showing a standard curve for ferric hydroxamate complex formed from a reaction of γ-glutamyl hydroxamate with $FeCl_3$ in an acidic medium, in the presence of reagents used for detection of GGHS catalytic activity.

A separate standard curve was plotted for the ferric hydroxamate complex formed in the presence of reagents used for GGHS catalytic activity by plotting the optical density of the colored product ferric hydroxamate on the y axis and the concentration of the γ-glutamyl hydroxamate in mM plotted on the x axis. FIG. 3 shows an exemplary standard curve for ferric hydroxamate complex formed from γ-glutamyl hydroxamate with FeCl$_3$ in acidic medium, in the presence of reagents used in GGHS catalytic activity. In reference to Equation 7, the equation of the graph for the standard curve is as follows:

$$y=(0.134x)-0.0015 \qquad \text{Eq. 12}$$

where y was the optical density at 500 nm of wavelength and x was the concentration of γ-glutamyl hydroxamate in mM. From the Equation 12, the concentration of γ-glutamyl hydroxamate in μM was derived as follows:

$$\gamma\text{-glutamyl hydroxamate in } \mu M = x = \frac{(y + 0.0015) \times 1000}{0.134} \qquad \text{Eq. 13}$$

Conversion of γ-Glutamyl Hydroxamate Concentrations to Catalytic Activities Expressed as Enzyme Units Per Liter L-GHGT and GGHS catalytic activities of the glutamine synthetase enzyme are expressed in microkatals as the number of micromoles of γ-glutamyl hydroxamate formed per second. This is then converted into Enzyme Units. One Enzyme Unit (Unit of catalytic activity)=1/60th of a microkatal. The L-GHGT and GGHS reactions in this example were carried out by incubating the reaction tubes for 5 minutes. Therefore, $$\text{Catalytic activites of } L\text{-}GHGT \text{ and } GGHS \text{ in} \qquad \text{Eq. 14}$$

$$\text{Enzyme Units } (U) = \frac{\gamma\text{-glutamyl hydroxamate in } \mu M}{60 \times 5 \times 60}$$

Since this reaction used 50 microliter of plasma, the following equation was used to express the L-GHGT and GGHS catalytic activities in Catalytic Units per Liter (U/L) of plasma.

$$= \frac{\gamma\text{-glutamyl hydroxamate in } \mu M \times 1000 \times 1000}{60 \times 5 \times 60 \times 50} \qquad \text{Eq. 15}$$

In reference to Equation 11, the catalytic activity of L-GHGT per liter of plasma was expressed in Enzyme units per liter (U/L) of plasma and was derived from the Equation 15 as follows:

$$= \frac{(y - 0.0087) \times 1000 \times 1000 \times 1000}{0.1402 \times 60 \times 5 \times 60 \times 50} \qquad \text{Eq. 16}$$

$$= (OD - 0.0087) \times 7925.19 U/L \qquad \text{Eq. 17}$$

In reference to Equation 13, the catalytic activity of GGHS per liter of plasma was expressed in Enzyme units per liter (U/L) of plasma can be derived from the Equation 15 as follows:

$$= \frac{(y + 0.0015) \times 1000 \times 1000 \times 1000}{0.134 \times 60 \times 5 \times 60 \times 50} \qquad \text{Eq. 18}$$

$$= (OD + 0.0015) \times 8291.87 U/L \qquad \text{Eq. 19}$$

Results:

After preparing the standard curve and standardizing the protocols using blood samples from patients, the diagnostic assays were carried out. Plasma samples were prepared from blood samples collected from forty nine patients who were brought to the Emergency departments with stroke symptoms (including transient ischemic attack (TIA)) and other acute neurological diseases that required ruling out of a stroke diagnosis. Of the forty nine patients, twenty nine patients were diagnosed with acute stroke (including TIA) using different diagnostic tools including clinical examination, clinical diagnostic laboratory tests, diagnostic imaging and electro-encephalographic recording when required, both during the arrival at the Emergency department and at later intervals. Twenty of these patients did not receive a stroke diagnosis based on the results generated with diagnostic tools including clinical examination, clinical diagnostic laboratory tests, diagnostic imaging and electro-encephalographic recording, and were designated as the "control group". The majority of the control group were admitted with stroke-like presentations from diseases that mimic stroke. After obtaining approval from the University of Manitoba Ethics committee and appropriate consent from the patients or their immediate family members, one milliliter of blood was collected in heparin tubes within four and a half hours from the beginning of the suspected stroke event and/or other acute neurological disorders. These plasma samples were tested for L-GHGT and GGHS catalytic activities.

Figure 4:
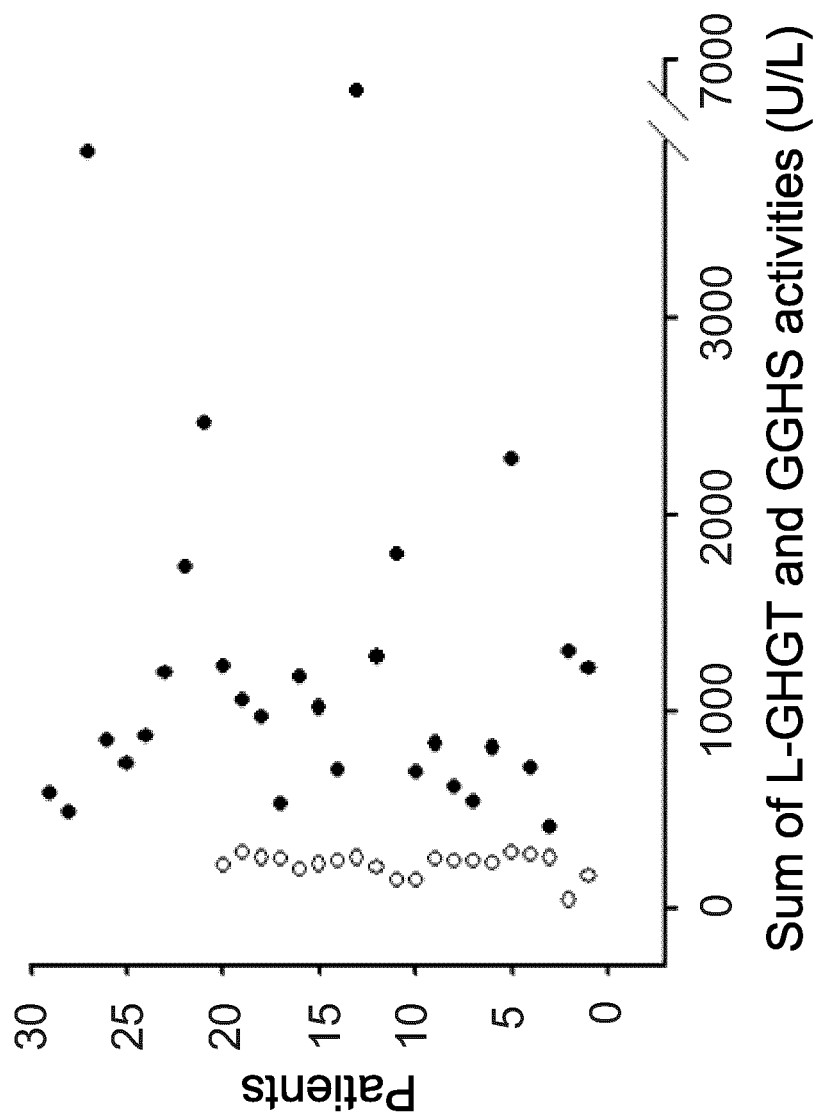
FIG. 4 is chart showing a scatter plot of the sums of L-GHGT activities and GGHS activities of glutamine synthetase enzyme in patients who experienced a clinically diagnosed stroke event (black circles), and in non-stroke patients (open circles)

For all forty nine patients, the L-GHGT catalytic activities and the GGHS catalytic activities of glutamine synthetase enzyme were measured using the assay protocols developed by the present disclosure. The sums of the L-GHGT activities and the GGHS activities were calculated following the steps and using the formulae disclosed herein. In patients who were clinically diagnosed with stroke (including TIA), the sums of L-GHGT activities and GGHS activities ranged between 405.49 U/L to 6616.03 U/L with a mean of 1328.73 (n=29 patients; s.e.m 231.93). In patients who were clinically diagnosed with diseases other than stroke, the sums of the L-GHGT activities and the GGHS activities ranged between 37.31 U/L to 277.82 U/L with a mean of 216.75 (n=20 patients; s.e.m 13.01). FIG. 4 is a scatter plot comparing the sums of L-GHGT activities and GGHS activities of glutamine synthetase enzyme in patients clinically diagnosed stroke with control patients who did not receive a clinical diagnosis of stroke. The sums of L-GHGT activities and GGHS activities in patients who were clinically diagnosed with stroke (including TIA) (n=29 patients) were significantly higher than in the control group (n=20 patients) (p<0.001) thereby confirming that the sums of L-GHGT catalytic activities and GGHS catalytic activities can be used as a diagnostic test for the detection of the occurrence of stroke events.

None of the patients who were clinically diagnosed with stroke had both L-GHGT levels and GGHS levels lower than the maximum values respectively for L-GHGT activities and GGHS activities among patients who were not clinically diagnosed with stroke. This observation indicates that glutamine synthetase enzyme leaked into the blood streams of stroke patients (including TIA) exists in different forms and provided high values of both L-GHGT activities and GGHS activities or alternatively, high values for either one of the above activities. This discovery makes it possible to calculate combinatorial probabilities to assess whether a stroke event has occurred with 99.9% confidence. Independent values for L-GHGT levels in the twenty nine patients who were clinically diagnosed with stroke (including TIA) ranged between 160.88 U/L and 3030 U/L. L-GHGT levels in the twenty control group patients who were clinically diagnosed with diseases but not a stroke event, ranged between 0 U/L and 240.13 U/L. Three patients who were clinically diagnosed with stroke had L-GHGT values lower than the maximum value of 240.13 U/L among patients who were clinically diagnosed with diseases other than stroke. GGHS levels in the twenty nine patients who were clinically diagnosed with stroke (including TIA) ranged between 29.02 U/L and 3586 U/L. GGHS levels in the twenty control group patients who were clinically diagnosed with diseases other than stroke ranged between 12.44 U/L and 45.61 U/L. One patient who was clinically diagnosed with stroke had GGHS level lower than the maximum value of 45.61 U/L obtained for GGHS levels among patients who were clinically diagnosed with diseases other than stroke.

Combinatorial probabilities to detect whether stroke is present or absent with 99.9% confidence using the derived values of the L-GHGT activities and GGHS activities, can be calculated. This can be used as an alternative approach to show the significance of the sum of the values of the L-GHGT and GGHS in diagnosing patients with stroke. Maximum value of L-GHGT activity among patients who were clinically diagnosed with diseases other than stroke was 240.13 U/L and maximum value of GGHS activity among patients who were clinically diagnosed with diseases other than stroke was 45.61 U/L.

Let X be random variable that represents the result of L-GHGT test. Let Y be random variable that represents the result of GGHS test.

Let $P(\text{disease}|X \geq 300) = 99.9\%$  Eq. 20

Let $P(\text{disease}|Y \geq 100) = 99.9\%$  Eq. 21

In normally distributed data, using z-score the following is obtained:

$P(z < -3.09) = 99.9\%$.  Eq. 22

From here, solving for mean and standard deviation for L-GHGT and GGHS results:

$$-3.09 = \frac{300 - \mu}{\sigma}$$  Eq. 23

Hence, by coinciding the L-GHST and GGHS results, we obtain $\mu = 97$ and $\sigma = 65$ by rounding to whole number, for L-GHGT test.
Similarly, for GGHS test $$-3.09 = \frac{100 - \mu}{\sigma}$$  Eq. 24

Hence, we obtain $\mu = -102$ and $\sigma = 65$ for GGHS test.
Finding $x_0$ and $y_0$ such that the following holds:

$P(\text{disease}|X \geq x_0 \wedge Y \geq y_0) \leq 100\% - 99.9\% = 0.1\%$  Eq. 25 or equivalently $P(X \geq x_0)P(Y \geq y_0) \leq 0.001$  Eq. 26 with the conditions $x_0 \geq 240.13$ and $y_0 \geq 45.61$
If the result of L-GHGT test of a patient is $x_0$, then to say that the patient has the disease with 99.9% confidence, the result of GGHS test of that patient must be greater or equal to the amount such that:

$$P\left(Z > \frac{x_0 - 97}{65}\right)P\left(Y \geq \frac{y_0 + 102}{65}\right) \leq 0.001$$  Eq. 27

For example, one of the stroke patients had L-GHGT activity=454.11 U/L and GGHS activity=29.02 U/L
Therefore, in the above equation, $x_0 = 454.11$; $y_0 = 29.02$
Converting to z-score:

$$P(X \geq 454.11) = P\left(Z \geq \frac{454.11 - 97}{65}\right) = P(Z > 5.49) \approx 10^{-7}$$  Eq. 28

$$P(Y \geq 29.02) = P\left(Z \geq \frac{29.02 + 102}{65}\right) = P(Z > 2) = 0.03$$  Eq. 29

Now, since $10^{-7} \times 0.03 < 0.001$, we can say with 99.9% confidence that the patient has stroke (including TIA).

All the combinations of the results for L-GHGT and GGHS tests for all the patients satisfied the above criteria and statements. Hence, a combination of the results for the L-GHGT catalytic activities and the GGHS catalytic activities provides a reliable diagnosis of a stroke event with 99.9% confidence. These data confirm that using probability distributions of values of the L-GHGT assays and the GGHS assays from large number of cases in the community, will enable determination of suitable cut-off values for diagnosing stroke events in a given community.

Figure 5:
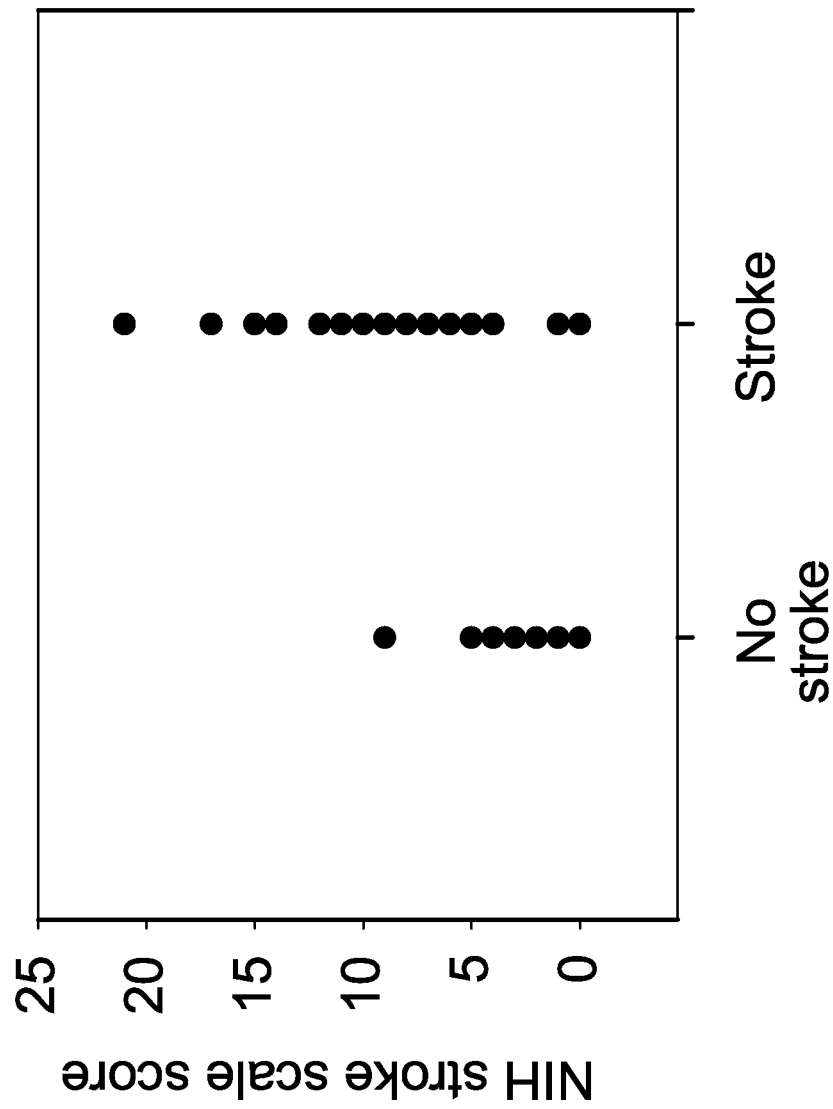
FIG. 5 is a chart showing the NIH stroke scale scores in patients who experienced a clinically diagnosed stroke, and in non-stroke control patients admitted with acute neurological diseases and diagnosed with conditions other than stroke.

The NIH stroke scale (NIHSS) scores is a clinical diagnostic tool for assessment of the severity of stroke symptoms. A normal person generally has a NIH stroke scale score of zero. Maximum NIH stroke scale score in severe stroke patient is 34. FIG. 5 is a chart showing the NIH stroke scale scores in patients clinically diagnosed stroke and in control patients (non-stroke) admitted with acute neurological diseases who were diagnosed with conditions other than stroke. Even though 100% of the clinically diagnosed stroke patients included in the study had a positive NIHSS score, many patients with clinical conditions other than stroke had elevated NIHSS scores of up to 10. Thus, the present biomarker assay is more highly correlated with clinically diagnosed stroke cases than are the NIHSS scores.

Figure 6:
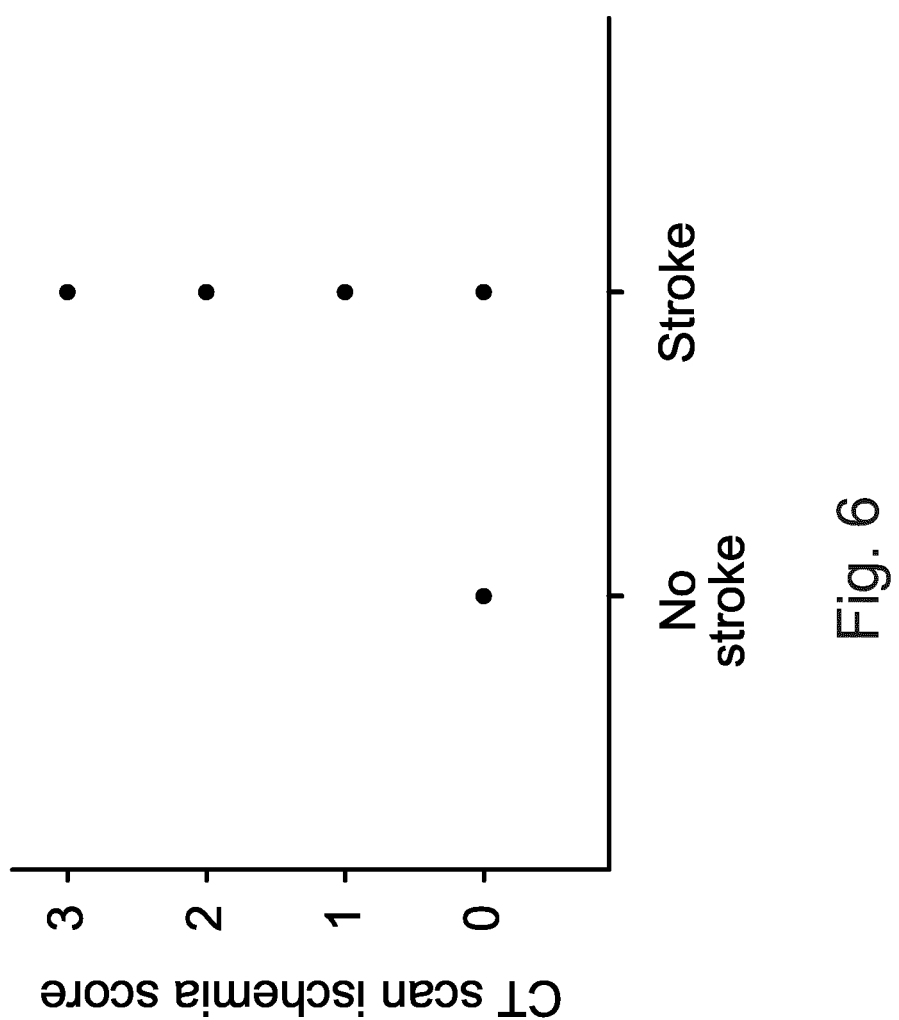
FIG. 6 is a chart showing CT scan ischemic scores in patients who experienced a clinically diagnosed stroke event, and in non-stroke control patients admitted with acute neurological diseases and diagnosed with conditions other than stroke.

A scoring system was devised to assess CT scan ischemic changes in 14 locations within the brain areas supplied by both anterior and posterior circulations providing 14 score points. One score each was given to each of the 10 locations used in Alberta Stroke Program Early Computed Tomography score (ASPECTs) scoring system (total 10 points) and one score each was given to ischemic changes in the anterior and posterior halves of the cerebellum on either sides (total 4 points). A person with normal brain perfusion at fourteen specific cortical areas in the anterior and posterior cerebral circulation was assigned a score of zero. Initial CT scan only showed changes of ischemia in approximately 17% of patients diagnosed clinically with stroke. FIG. 6 is a chart showing CT scan ischemic scores in patients that were clinically diagnosed with stroke and with other acute non-stroke neurological diseases. These data show that even though the CT scan changes observed in ischemic stroke are specific, CT scans are less useful for detecting stroke in emergency settings. This finding in combination with the results of the present biomarker assay strongly indicate that plasma L-GHGT and GGHS activities of the glutamine synthetase enzyme are highly useful than CT scan findings in the diagnosis of the occurrence of an acute stroke.

The results show that sum of L-GHGT and GGHS catalytic activities of glutamine synthetase enzyme above certain specific values is diagnostic of stroke (including TIA). The results of this work also show that catalytic activities detected with the present L-GHGT and GGHS biomarker assays are more precise than NIHSS scores and observed CT scan ischemic changes, for diagnosing stroke events. The present disclosure shows that L-GHGT and GGHS biomarker assays of the glutamine synthetase enzyme can complement CT scan results for the diagnosis and management of stroke. The present disclosure can be used as a surrogate diagnostic test for stroke and has the potential to provide biomarker-based point of care algorithm. In summary, the present disclosure can be applied to determine population ranges for the L-GHGT and GGHS catalytic activities of the glutamine synthetase enzyme in the plasma samples from both stroke and control patients and can be used as standard biomarker assay to diagnose stroke in the community.

The present disclosure also pertains to kits useful for rapid detection of stroke events. For example, a kit may comprise a set of reagent stock solutions as described herein and optionally instructions for their use. Kits may further comprise instructional material with step-by-step methods teaching how to use the materials provided in the kits for performing and quantifying the L-GHGT activity assays and GGHS activity assays in plasma separated from blood samples. Kits may also comprise one or more devices for collecting blood samples from a mammalian subject. Kits may also comprise one or more devices for separating plasma fractions from the blood samples. Kits may also comprise a color intensity scale or alternatively, a color intensity reader/recorder for measuring and/or recording color intensity in processed plasma samples.

Kits may comprise a container with a label. Suitable containers include, for example, bottles, vials, and test tubes. The containers may be made from a variety of materials such as glass or plastic. The label on the container may indicate that the composition is used for a specific diagnosis, and may also indicate directions for uses such as those described above. The kit of the disclosure will typically comprise the container described above and one or more other containers comprising materials desirable from a commercial and user standpoint, including buffers, diluents, filters, needles, syringes, and package inserts with instructions for use.

Some exemplary embodiments pertain to emergency response kits for use in detecting an occurrence of a stroke event. The kits may comprise at least stock solutions for one of the L-GHGT activity assay and the GGHS activity assay. The kits may comprise stock solutions for both the L-GHGT assay and the GGHS assay. Exemplary reagent solutions for the L-GHGT activity assay may comprise: (i) pH 6.5 imidazole buffer (0.5 M), (ii) $NH_2OH$ (0.4 M), (iii) L-glutamine (0.1 M), (iv) $MnCl_2$ (0.03 M), (v) NaADP (0.01 M), (vi) L-methionine sulfoximine (0.05M), (vii) HCl (2 N), and (vii) $FeCl_3$ (2 M). Exemplary reagent solutions for the GGHS activity assay may comprise: (i) pH 7.2 imidazole buffer (0.5 M), (ii) $NH_2OH$ (0.4 M), (iii) L-glutamate (0.05 M), (iv) MgATP (0.02 M), (v) L-methionine sulfoximine (0.05 M), (vi) HCl (2 N), and (vii) $FeCl_3$ (2 M). The reagents may be provided in a dry form or in a solution form.

An exemplary diagnostic kit for detecting a L-GHGT activity in a plasma fraction separated from a blood sample collected from a mammalian subject, may optionally comprise a plurality of sets of the reagent mixtures. The kit may additionally contain one or more lithium heparin tubes for receiving the reagent mixtures, and for performing the L-GHGT assay therein. The kit may additionally comprise one or more devices for collecting a blood sample from an individual. The kit may additionally comprise one or more devices for separating plasma fractions from the blood samples. The kit may additionally comprise a color intensity scale or alternatively, a color intensity reader/recorder for measuring and/or recording color intensity in processed plasma samples.

An exemplary diagnostic kit for detecting a GGHS activity in a plasma fraction separated from a blood sample collected from a mammalian subject, may optionally comprise a plurality of sets of the reagent mixtures. The kit may additionally contain one or more lithium heparin tubes for receiving the reagent mixtures, and for performing the GGHS assay therein. The kit may additionally comprise one or more devices for collecting a blood sample from an individual. The kit may additionally comprise one or more devices for separating plasma fractions from the blood samples. The kit may additionally comprise a color intensity scale or alternatively, a color intensity reader/recorder for measuring and/or recording color intensity in processed plasma samples.

The invention claimed is:

1. A diagnostic assay for detecting an occurrence of a stroke event in a mammalian subject, comprising:
   (1) separating a plasma fraction from a blood sample collected from the mammalian subject;
   (2) quantifying in the plasma fraction a L-glutamine hydroxylamine glutamyl transferase (L-GHGT) activity detected with an assay comprising three sets of steps wherein
   the first set of steps comprises
      (i) mixing together a pH 6.5 imidazole buffer, a $NH_2OH$ solution, a $MnCl_2$ solution, a Na-ADP solution, and a L-glutamine solution to form a first mixture;
      (ii) mixing together the first mixture with water to form a second mixture;
      (iii) mixing together the second mixture with an aliquot of the plasma fraction to form a third mixture;
      (iv) incubating the third mixture at about 30° C. for production therein of a L-glutamic acid γ-monohydroxamate product;
      (v) mixing together the incubated third mixture with a L-methionine sulfoximine solution and a hydrochloric acid solution to form a fourth mixture;
      (vi) mixing together the fourth mixture with a ferric chloride solution to form a fifth mixture;
      (vii) incubating the fifth mixture at about 37° C. for production therein of a ferric hydroxamate complex; and
      (viii) measuring the optical density of the fifth mixture at an excitation wavelength of about 500 nm to produce a first optical density;
   the second set of steps comprises
      (ix) mixing together a pH 6.5 imidazole buffer, a $NH_2OH$ solution, a $MnCl_2$ solution, a Na-ADP solution, and a L-glutamine solution to form a sixth mixture;
      (x) mixing together the sixth mixture with a L-methionine sulfoximine solution and a hydrochloric acid solution to form a seventh mixture;
      (xi) mixing together the seventh mixture with an aliquot of the plasma fraction to form an eighth mixture;
      (xii) incubating the eighth mixture at about 30° C. for production therein of a control reaction;
      (xiii) mixing together the incubated eighth mixture with water to form a ninth mixture;
      (xiv) mixing together mixture;
      (xv) incubating the tenth mixture at about 37° C. for production therein of a ferric hydroxamate complex; and
      (xvi) measuring the optical density of the tenth mixture at an excitation wavelength of about 500 nm to produce a second optical density wherein said second optical density is a control optical density; and
   the third set of steps comprises
      (xvii) subtracting the second optical density from the first optical density of the fifth mixture to produce a third optical density; and
      (xviii) correlating the third optical density to a L-GHGT activity of glutamine synthetase enzyme and expressing said L-GHGT activity in Units per liter of plasma;
   (3) quantifying in the plasma fraction a gamma glutamyl hydroxamate synthetase (GGHS) activity detected with an assay comprising three sets of steps wherein
   the first set of steps comprises
      (xix) mixing together a pH 7.2 imidazole buffer, a $NH_2OH$ solution, a Mg-ATP solution, and a L-glutamine solution to form a first mixture;

(xx) mixing together the first mixture with water to form a second mixture;

(xxi) mixing together the second mixture with an aliquot of the plasma fraction to form a third mixture;

(xxii) incubating the third mixture at about 37° C. for production therein of a L-glutamic acid γ-monohydroxamate product;

(xxiii) mixing together the incubated third mixture with a L-methionine sulfoximine solution and a hydrochloric acid solution to form a fourth mixture;

(xxiv) mixing together the fourth mixture with a ferric chloride solution to form a fifth mixture;

(xxv) incubating the fifth mixture at about 37° C. for production therein of a ferric hydroxamate complex; and (xxvi) measuring the optical density of the fifth mixture at an excitation wavelength of about 500 nm to produce a first optical density;

the second set of steps comprises (xxvii) mixing together (x) a pH 7.2 imidazole buffer, a $NH_2OH$ solution, a Mg-ATP solution, and a L-glutamine solution to form a sixth mixture;

(xxviii) mixing together the sixth mixture with a L-methionine sulfoximine solution and a hydrochloric acid solution to form a seventh mixture;

(xxix) mixing together the seventh mixture with an aliquot of the plasma fraction to form an eighth mixture;

(xxx) incubating the eighth mixture at about 37° C. for production therein of a control reaction;

(xxxi) mixing together the incubated eighth mixture with water to form a ninth mixture;

(xxxii) mixing together the ninth mixture with a ferric chloride solution to form a tenth mixture;

(xxxiii) incubating the tenth mixture at about 37° C. for production therein of a ferric hydroxamate complex; and (xxxiv) measuring the optical density of the tenth mixture at an excitation wavelength of about 500 nm to produce a second optical density wherein said second optical density is a control optical density; and the third set of steps comprises (xxxv) subtracting the second optical density from the first optical density of the fifth mixture to produce a third optical density; and (xxxvi) correlating the third optical density to a GGHS activity of glutamine synthetase enzyme and expressing said GGHS activity in Units per liter of plasma;

(4) producing a value for glutamine synthetase activity by adding together the quantified L-GHGT activity and the quantified GGHS activity or alternatively, by estimating combinatorial probabilities of the quantified L-GHGT activity and the quantified GGHS activity; and (5) correlating said glutamine synthetase activity value with a glutamine synthetase activity value from a healthy subject to detect an occurrence of a stroke event.

2. A diagnostic assay kit for detecting a L-GHGT activity in a plasma fraction separated from a blood sample collected from a mammalian subject, comprising:
a pH 6.5 imidazole buffer;
a $NH_2OH$ solution;
a $MnCl_2$ solution;
a Na-ADP solution;
a L-glutamine solution;
L-methionine sulfoximine solution;
a hydrochloric acid solution;
a $FeCl_3$ solution; and
a set of directions for use of said solutions to process said plasma fraction.

3. A diagnostic assay kit according to claim 2, additionally comprising a tube consisting of lithium heparin for receiving a blood sample therein and performing the assay therein.

4. A diagnostic assay kit for detecting a GGHS activity in a plasma fraction separated from a blood sample collected from a mammalian subject, comprising:
a pH 7.2 imidazole buffer;
a $NH_2OH$ solution;
a Mg-ATP solution;
a L-glutamate solution;
L-methionine sulfoximine solution;
a hydrochloric acid solution;
a $FeCl_3$ solution; and
a set of directions for use of said solutions to process said plasma fraction.

5. A diagnostic assay kit according to claim 4, additionally comprising a tube consisting of lithium heparin for receiving a blood sample therein and performing the assay therein.

* * * * *